(12) United States Patent
Miller (10) Patent No.: US 7,452,372 B2
(45) Date of Patent: Nov. 18, 2008

(54) BIFURCATED STENT

(75) Inventor: Matthew J. Miller, Stillwater, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 245 days.

(21) Appl. No.: 11/232,681

(22) Filed: Sep. 22, 2005

(65) Prior Publication Data

US 2007/0067018 A1 Mar. 22, 2007

(51) Int. Cl.
*A61F 2/06* (2006.01)
(52) U.S. Cl. .................................................. 623/1.35
(58) Field of Classification Search ............... 623/1.15, 623/1.16, 1.35, 1.44, 1.46
See application file for complete search history.

(56) References Cited

U.S. PATENT DOCUMENTS

| | | | | |
|---|---|---|---|---|
| 5,752,935 | A | 5/1998 | Robinson et al. | 604/97 |
| 5,855,565 | A | 1/1999 | Bar-Cohen et al. | 604/104 |
| 5,873,907 | A | 2/1999 | Frantzen | 623/1 |
| 6,090,139 | A * | 7/2000 | Lemelson | 623/2.1 |
| 6,123,718 | A | 9/2000 | Tu et al. | 607/113 |
| 6,171,609 | B1 * | 1/2001 | Kunz | 424/422 |
| 6,203,568 | B1 * | 3/2001 | Lombardi et al. | 623/1.13 |
| 6,249,076 | B1 | 6/2001 | Madden et al. | 310/363 |
| 6,514,237 | B1 | 2/2003 | Maseda | 604/533 |
| 6,515,077 | B1 | 2/2003 | Su et al. | 525/276 |
| 6,545,391 | B1 | 4/2003 | Su et al. | 310/332 |
| 6,579,309 | B1 | 6/2003 | Loos et al. | 623/1.16 |
| 6,664,718 | B2 | 12/2003 | Pelrine et al. | 310/800 |
| 6,679,836 | B2 | 1/2004 | Couvillon, Jr. | 600/146 |
| 6,706,062 | B2 | 3/2004 | Vardi et al. | 623/1.15 |
| 6,749,556 | B2 | 6/2004 | Banik | 600/30 |
| 6,770,027 | B2 | 8/2004 | Banik et al. | 600/146 |
| 6,835,173 | B2 | 12/2004 | Couvillon, Jr. | 600/146 |
| 6,921,360 | B2 | 7/2005 | Banik | 600/30 |
| 2002/0058993 | A1 * | 5/2002 | Landau et al. | 623/1.35 |

(Continued)

FOREIGN PATENT DOCUMENTS

EP 0619749 10/1994

(Continued)

OTHER PUBLICATIONS

D. Zhou et al., "Actuators for the Cochlear Implant," *Synthetic Metals* 135-136 (2003) 39-40.

(Continued)

*Primary Examiner*—William H. Matthews
*Assistant Examiner*—Suba Ganesan
(74) *Attorney, Agent, or Firm*—Vidas, Arrett & Steinkraus (57) ABSTRACT

A stent for placement at a vessel bifurcation has an expanded configuration and an unexpanded configuration. The stent comprises a substantially tubular main body and a branch body. The branch body comprises at least one flexible member engaged to the main body. The flexible member comprises an expandable polymer which is actuatable between a high volume state and a low volume state. When in the high volume state the volume of the expandable polymer is greater than in the low volume state. Also, when the expandable polymer is actuated from the low volume state to the high volume state, the branch body is expanded from the unexpanded configuration to the expanded configuration. In the expanded configuration the branch body extends obliquely from the main body.

12 Claims, 4 Drawing Sheets

U.S. PATENT DOCUMENTS

| | | | |
|---|---|---|---|
| 2002/0188341 A1 | 12/2002 | Elliott | 623/1.1 |
| 2002/0193873 A1 | 12/2002 | Brucker et al. | 623/1.35 |
| 2003/0099684 A1 | 5/2003 | Domb | 424/426 |
| 2003/0236445 A1 | 12/2003 | Couvillon, Jr. | 600/114 |
| 2004/0068161 A1 | 4/2004 | Couvillon, Jr. | 600/143 |
| 2004/0087982 A1 | 5/2004 | Eskuri | 606/153 |
| 2004/0138737 A1 | 7/2004 | Davidson et al. | 623/1.35 |
| 2004/0143160 A1 | 7/2004 | Couvillon, Jr. | 600/114 |
| 2004/0182704 A1* | 9/2004 | Daunert et al. | 204/405 |
| 2004/0248269 A1 | 12/2004 | Cinquin et al. | 435/183 |
| 2005/0004425 A1 | 1/2005 | Banik | 600/30 |
| 2005/0010278 A1 | 1/2005 | Vardi et al. | 623/1.15 |
| 2005/0102017 A1 | 5/2005 | Mattison | 623/1.11 |
| 2005/0119213 A1 | 6/2005 | Khachigian | 514/44 |
| 2005/0165439 A1 | 7/2005 | Weber et al. | 606/191 |
| 2005/0183259 A1 | 8/2005 | Eidenschink et al. | 29/508 |

FOREIGN PATENT DOCUMENTS

| | | | |
|---|---|---|---|
| WO | WO 9625897 | * | 8/1996 |
| WO | WO 03/030727 | | 4/2003 |
| WO | WO 2005/009295 | | 2/2005 |

OTHER PUBLICATIONS

E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir*, 14 (11), 3970-3975, 1998.

E.W.H. Jager, E. Smela, O. Inganas, "Microfabricating Conjugated Polymer Actuators," *Science*, 290, 1540-1545, 2000.

E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999.

*Proceedings of the SPIE*, vol. 4329 (2001) entitled "Smart Structures and Materials" 2001. see Madden et al., "Polypyrrole actuators: modeling and performance," pp. 73-83.

Yoshioka et al., "Epoxy-based Electroactive Polymer Gels," vol. 42, no. 4, pp. 404-408, Dec. 2002.

* cited by examiner

FIG. 16

BIFURCATED STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. § 1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a stent for placement at the site of a vessel bifurcation. That is, where a vessel has a main branch as well as a side branch. U.S. patent application Ser. No. 09/963,114, filed on Sep. 24, 2001, U.S. patent application Ser. No. 10/644,550, filed on Aug. 21, 2003, and U.S. patent application Ser. No. 10/910, 598, filed Aug. 4, 2004, the entire contents of which being incorporated herein by reference, describe bifurcated stents.

In at least one embodiment, the bifurcated stent has an expanded and unexpanded configuration. The stent has a substantially tubular main body which defines a main lumen therethrough, and a branch body which defines a branch lumen therethrough. The main lumen and the branch lumen are in fluid communication. The branch body comprises at least one flexible member engaged to the main body. The at least one flexible member is comprised of an expandable polymer which is actuatable between a high volume state and a low volume state such that when in the high volume state the volume of the expandable polymer is greater than in the low volume state. When the expandable polymer is actuated from the low volume state to the high volume state, the branch body is expanded from the unexpanded configuration to the expanded configuration. In the expanded configuration, the branch body extends obliquely from the main body.

In some embodiments the expandable polymer comprises an electroactive polymer.

In some embodiments, the expandable polymer includes a coating that fissures (a fissurable coating). In some embodiments the fissurable coating fissures upon initial deployment of the stent. In other embodiments, the stent is in an unexpanded configuration coated with the fissurable coating, and once the fissurable coating fissures, the expandable polymer actuates from the low volume state to the high volume state, expanding the stent to the expanded configuration. In at least one embodiment, the fissurable coating fissures after interacting with a fluid introduced into the body after the stent body is placed at the vessel bifurcation. In at least one embodiment, the expandable polymer is expanded by interacting with a fluid, the fluid introduced into the body after the stent body is placed at the vessel bifurcation.

In at least one embodiment, the bifurcated stent has an expanded configuration and an unexpanded configuration. The stent has a substantially tubular main body which defines a main lumen therethrough, and a branch body which defines a branch lumen therethrough. The main lumen and the branch lumen are in fluid communication. The branch body comprises a first flexible member and a second flexible member, and a connector engaged to the first flexible member. The branch body is in the unexpanded state when the connector is engaged to the second flexible member, and the branch body is in the expanded state when the second flexible member is disengaged from the connector.

In some embodiments the connector is electrically frangible. That is, the connector is capable of being broken upon delivery of electric current. A first flexible member is engaged to a second flexible member by the connector when the stent is in the unexpanded configuration. When the electrically frangible connector is broken, the stent expands to the expanded configuration.

In at least one embodiment the electrically frangible connector is a fusible link. In some embodiments the electrically frangible connector is an electrolytic conductor. In at least one embodiment the electrically frangible connector is a switch.

In some embodiments the connector is magnetically frangible such that the first flexible member is magnetically coupled to the second flexible member by the connector when the stent is in the unexpanded configuration. The first flexible member is magnetically decoupled from the second flexible member when the stent is in the expanded configuration.

In some embodiments the connector is fixedly engaged to a first flexible member and when the stent is in the unexpanded state the connector is releasably engaged to a second flexible member. When the stent is in the expanded configuration the connector is disengaged from the second flexible member.

The present invention also contemplates embodiments of methods of deploying a bifurcated stent to a vessel bifurcation. In at least one embodiment, a bifurcated stent is advanced through a body lumen to the vessel bifurcation. The stent has a substantially tubular main body which defines a main lumen therethrough, and a branch body which defines a branch lumen therethrough. The main lumen and the branch lumen are in fluid communication. The branch body comprises at least one flexible member engaged to the main body. The at least one flexible member is comprised of an expandable polymer which is actuatable between a high volume state and a low volume state such that when in the high volume state the volume of the expandable polymer is greater than in the low volume state. When the expandable polymer is actuated from the low volume state to the high volume state, the branch body is expanded from the unexpanded configuration to the expanded configuration. In the expanded configuration, the branch body extends obliquely from the main body. The method further includes the step of aligning the branch body with the side branch. Then, actuating the expandable polymer from the low volume state to the high volume state.

In some embodiments the expandable polymer is comprised of an electroactive polymer (EAP). The method of deploying a bifurcated stent with an expandable polymer comprised of EAP further includes the steps of connecting electrodes to the electroactive polymer, adhering the electrodes and electroactive polymer to the at least one flexible member, and then applying a voltage across the electrodes to the electroactive polymer.

In at least one embodiment, the method of deployment comprises the step of introducing a fluid into the body after the branch body is placed at the side branch of the vessel, whereupon the expandable polymer expands by interacting with the fluid. The fluid is the trigger mechanism for expanding the expandable polymer.

In some embodiments, the method of deployment further comprises the step of coating the expandable polymer with a fissurable coating, and fissuring the fissurable coating during initial stent deployment. In some embodiments, the fissurable coating fissures as a result of introducing a fluid into the body after the stent has been placed at the vessel bifurcation.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

Figure 1:
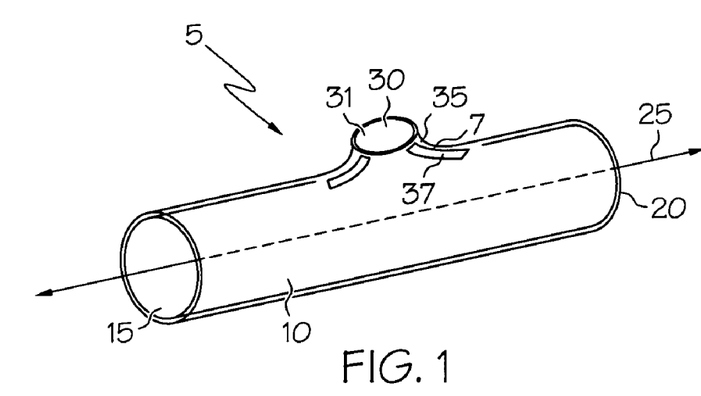
FIG. 1 is a perspective view of an embodiment of the invention, comprising a branch body and flexible members in a partially expanded configuration.

Referring now to the drawings, which are intended to illustrate embodiments of the invention only and not for the purpose of limiting same, in at least one embodiment of the invention, an example of which is shown in FIG. 1, a bifurcated stent, shown generally at 5, comprises a main body 10 with branch body 30. The main body 10 includes a proximal end 15, a distal end 20, and defines a main lumen 25 therebetween. Furthermore, the branch body 30 defines a branch lumen 31 such that the branch lumen 31 is in fluid communication with the main lumen 25. The bifurcated stent 5 further includes a petal 7, comprised of flexible member 35 with expandable polymer 37, shown in FIG. 1 in an unexpanded configuration. Each flexible member 35 is engaged to an expandable polymer 37. Expandable polymer 37 is actuatable between a high volume state and a low volume state such that when the expandable polymer 37 is in the high volume state, the volume of the expandable polymer is greater than in the low volume state. Also, each flexible member 35 is engaged to the main body 10 such that when expandable polymer 37 is expanded into the high volume state, flexible member 35 along with branch body 30 is expanded from the unexpanded configuration to the expanded configuration. Branch body 30 is shown in FIG. 1 in an unexpanded configuration with expandable polymer 37 shown in a low volume state.

Figure 2:
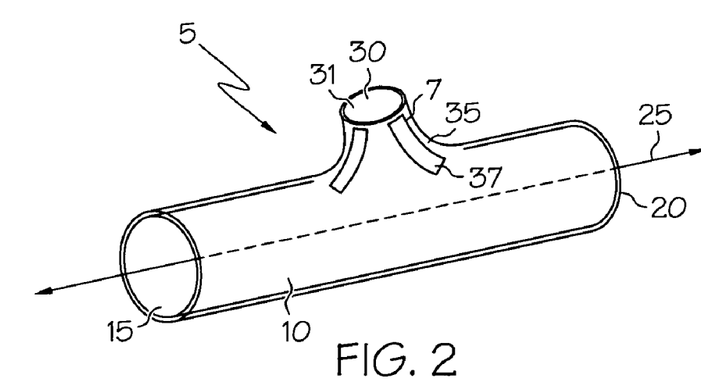
FIG. 2 is a perspective view of an embodiment of the invention, comprising a branch body and flexible members in an expanded configuration.

FIG. 2 shows the bifurcated stent of FIG. 1, but with branch body 30 in an expanded configuration. In the expanded configuration shown in FIG. 2, expandable polymer 37, engaged to flexible member 35, is in a high volume state.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Figure 3:
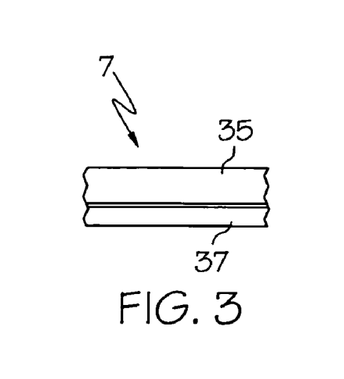
FIG. 3 is a side view of a portion of a petal comprised of a flexible member and an expandable polymer.

FIG. 3 depicts a side view of a portion of a petal, shown generally at 7, comprised of flexible member 35 with expandable polymer 37 engaged thereto. Expandable polymer 37 is in a low volume state in FIG. 3.

Figure 4:
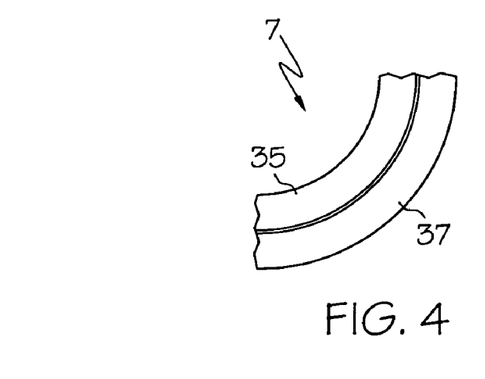
FIG. 4 is a side view of a portion of a petal comprised of a flexible member and an expandable polymer.

FIG. 4 shows a side view of the petal 7 of FIG. 3, with flexible member 35 and expandable polymer 37, but with expandable polymer 37 expanded to a high volume state. Flexible member 35 may deflect when expandable polymer 37 expands from a low volume state to a high volume state, as shown in FIG. 4. Expandable polymer 37 may be expanded by a fluid (not shown) introduced into the body after the stent has been placed at the vessel bifurcation.

Figure 5:
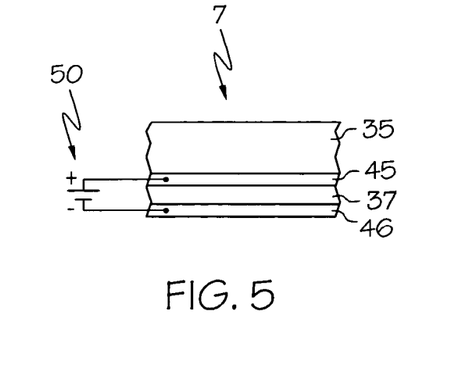
FIG. 5 is a side view of a portion of a petal comprised of a flexible member and an expandable polymer comprised of an electroactive polymer.

In FIG. 5, an expandable polymer 37 comprised of an electroactive polymer (EAP) is depicted. An electroactive polymer refers to a polymer that acts as an insulating dielectric between two electrodes and may deflect upon application of a voltage difference between the two electrodes. Electroactive polymers (EAP) are materials such as polypyrrole, polyalanine, polyacetylene, polythiophene and polyvinylidene difluoride (PVDF), etc. that show shape deformation when an electric field is applied. Electroactive polymer materials can be manufactured such that when there is a voltage difference between the two electrodes, the EAP material increases in volumetric size. Alternatively, the EAP material can be manufactured such that when there is a voltage difference between the two electrodes, the material decreases in volumetric size. When an electric field is applied across the EAP, the EAP deforms as a result of stresses generated by the movement of water and mobile positive ions in the polymer.

Electroactive polymers are characterized by their ability to change shape in response to electrical stimulation. EAPs include electric EAPs and ionic EAPs. Piezoelectric materials may also be employed but tend to undergo small deformation when voltage is applied.

Electric EAPs include ferroelectric polymers, dielectric EAPs, electrorestrictive polymers such as the electrorestrictive graft elastomers and electro-viscoelastic elastomers, and liquid crystal elastomer materials.

Ionic EAPs include ionic polymer gels, ionomeric polymer-metal composites, conductive polymers and carbon nanotubes. Upon application of a small voltage, ionic EAPs can bend significantly. Ionic EAPs also have a number of additional properties that make them attractive for use in the devices of the present invention, including the following: (a) they are lightweight, flexible, small and easily manufactured; (b) energy sources are available which are easy to control, and energy can be easily delivered to the EAPS; (c) small changes in potential (e.g., potential changes on the order of 1 V) can be used to effect volume change in the EAPs; (d) they are relatively fast in actuation (e.g., full expansion/contraction in a few seconds); (e) EAP regions can be created using a variety of techniques, for example, electrodeposition; and (f) EAP regions can be patterned, for example, using photolithography, if desired.

Conductive plastics may also be employed. Conductive plastics include common polymer materials which are almost exclusively thermoplastics that require the addition of conductive fillers such as powdered metals or carbon (usually carbon black or fiber).

Ionic polymer gels are activated by chemical reactions and can become swollen upon a change from an acid to an alkaline environment.

Ionomeric polymer-metal composites can bend as a result of the mobility of cations in the polymer network. Suitable base polymers include perfluorosulfonate and perfluorocarboxylate.

Essentially any electroactive polymer that exhibits contractile or expansile properties may be used in connection with the various active regions of the invention, including any of those listed above.

In some embodiments herein, the EAPs employed are ionic EAPs, more specifically, the ionic EAPs are conductive polymers that feature a conjugated backbone (they include a backbone that has an alternating series of single and double carbon-carbon bonds, and sometimes carbon-nitrogen bonds, i.e. π-conjugation) and have the ability to increase the electrical conductivity under oxidation or reduction. For polymers allows freedom of movement of electrons, therefore allowing the polymers to become conductive. The pi-conjugated polymers are converted into electrically conducting materials by oxidation (p-doping) or reduction (n-doping).

The volume of these polymers changes dramatically through redox reactions at corresponding electrodes through exchanges of ions with an electrolyte. The EAP-containing active region contracts of expands in response to the flow of ions out of, or into, the same. These exchanges occur with small applied voltages and voltage variation can be used to control actuation speeds.

Any of a variety of pi-conjugated polymers may be employed herein. Examples of suitable conductive polymers include, but are not limited to, polypyrroles, polyanilines, polythiophenes, polyethylenedioxythiophenes, poly(p-phenylenes), poly(p-phenylene vinylene)s, polysulfones, polypyridines, polyquinoxalines, polyanthraquinones, poly(N-vinylcarbazole)s and polyacetylenes, with the most commone being polythiophenes, polyanilines, and polypyrroles.

Some of the structures are shown below:

Polypyrrole, shown in more detail below, is one of the most stable of these polymers under physiological conditions:

The above list is intended for illustrative purposes only, and not as a limitation on the scope of the present invention.

The behavior of conjugated polymers is dramatically altered with the addition of charge transfer agents (dopants). These materials can be oxidized to a p-type doped material by doping with an anionic dopant species or reducible to a n-type doped material by doping with a cationic dopant species. Generally, polymers such as polypyrrole (PPy) are partially oxidized to produce p-doped materials:

Dopants have an effect on this oxidation-reduction scenario and convert semi-conducting polymers to conducting versions close to metallic conductivity in many instances. Such oxidation and reduction are believed to lead to a charge imbalance that, in turn, results in a flow of ions into or out of the material. These ions typically enter/exit the material from/into an ionically conductive electrolyte medium associated with the electroactive polymer.

Dimensional or volumetric changes can be effectuated in certain polymers by the mass transfer of ions into or out of the polymer. This ion transfer is used to build conductive polymer actuators (volume change). For example, in some conductive polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses (e.g., on the order of 1 MPa) and strains (e.g., on the order of 10%). These characteristics are ideal for construction of the devices of the present invention. As used herein, the expansion or the contraction of the active region of the device is generally referred to as "actuation."

The following elements are commonly utilized to bring about electroactive polymer actuation: (a) a source of electrical potential, (b) an active region, which comprises the electroactive polymer, (c) a counter electrode and (d) an electrolyte in contact with both the active region and the counter electrode.

The source of electrical potential for use in connection with the present invention can be quite simple, consisting, for example, of a dc battery and an on/off switch. Alternatively, more complex systems can be utilized. For example, an electrical link can be established with a microprocessor, allowing a complex set of control signals to be sent to the EAP-containing active region(s).

The electrolyte, which is in contact with at least a portion of the surface of the active region, allows for the flow of ions and thus acts as a source/sink for the ions. Any suitable electrolyte may be employed herein. The electrolyte may be, for example, a liquid, a gel, or a solid, so long as ion movement is permitted. Examples of suitable liquid electrolytes include, but are not limited to, an aqueous solution containing a salt, for example, an NaCl solution, a KCl solution, a sodium dodecylbenzene sulfonate solution, a phosphate buffered solution, physiological fluid, etc. Examples of suitable gel electrolytes include, but are not limited to, a salt-containing agar gel or polymethylmethacrylate (PMMA) gel. Solid electrolytes include ionic polymers different from the EAP and salt films.

The counter electrode may be formed from any suitable electrical conductor, for example, a conducting polymer, a conducting gel, or a metal, such as stainless steel, gold or platinum. At least a portion of the surface of the counter electrode is generally in contact with the electrolyte, in order to provide a return path for charge.

In one specific embodiment, the EAP employed is polypyrrole. Polypyrrole-containing active regions can be fabricated using a number of known techniques, for example, extrusion, casting, dip coating, spin coating, or electro-polymerization/deposition techniques. Such active regions can also be patterned, for example, using lithographic techniques, if desired.

As a specific example of a fabrication technique, polypyrrole can be galvanostatically deposited on a platinised substrate from a pyrrole monomer solution using the procedures described in D. Zhou et al., "Actuators for the Cochlear Implant," *Synthetic* Metals 135-136 (2003) 39-40. Polypyrrole can also be deposited on gold. In some embodiments, adhesion of the electrodeposited polypyrrole layer is enhanced by covering a metal such as gold with a chemisorbed layer of molecules that can be copolymerized into the polymer layer with chemical bonding. Thiol is one example of a head group for strong chemisorbtion to metal. The tail group may be chemically similar to structured groups formed in the specific EAP employed. The use of a pyrrole ring attached to a thiol group (e.g., via a short alkyl chain) is an example for a polypyrrole EAP. Specific examples of such molecules are 1-(2-thioethyl)-pyrrole and 3-(2-thioethyl)-pyrrole. See, e.g., E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir,* 14 (11), 2970-2975, 1998.

Various dopants can be used in the polypyrrole-containing active regions, including large immobile anions and large immobile cations. According to one specific embodiment, the active region comprises polypyrrole (PPy) doped with dodecylbenzene sulfonate (DBS) anions. When placed in contact with an electrolyte containing small mobile cations, for example, $Na^+$ cations, and when a current is passed between the polypyrrole-containing active region and a counter electrode, the cations are inserted/removed upon reduction/oxidation of the polymer, leading to expansion/contraction of the same. This process can be represented by the following equation:

$$PPY^+(DBS^-)+Na^++e^- \leftrightarrows PPy^\circ(Na^+DBS^-)$$

where $Na^+$ represents a sodium ion, $e^-$ represents an electron, $PPy^+$ represents the oxidized state of the polypyrrole, $PPy^\circ$ represents the reduced state of the polymer, and species are enclosed in parentheses to indicate that they are incorporated into the polymer. In this case the sodium ions are supplied by the electrolyte that is in contact with the electroactive polymer member. Specifically, when the EAP is oxidized, the positive charges on the backbone are at least partially compensated by the $DBS^-$ anions present within the polymer. Upon reduction of the polymer, however, the immobile $DBS^-$ ions cannot exit the polymer to maintain charge neutrality, so the smaller, more mobile, $Na^+$ ions enter the polymer, expanding the volume of the same. Upon re-oxidation, the $Na^+$ ions again exit the polymer into the electrolyte, reducing the volume of the polymer.

EAP-containing active regions can be provided that either expand or contract when an applied voltage of appropriate value is interrupted depending, for example, upon the selection of the EAP, dopant, and electrolyte.

Additional information regarding EAP actuators, their design considerations, and the materials and components that may be employed therein, can be found, for example, in E. W. H. Jager, E. Smela, O. Inganäs, "Microfabricating Conjugated Polymer Actuators," *Science,* 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems,* 8(4), 373-383, 1999; U.S. Pat. No. 6,249,076, assigned to Massachusetts Institute of Technology, and *Proceedings of the SPIE,* Vol. 4329 (2001) entitled "Smart Structures and Materials 2001: Electroactive Polymer and Actuator Devices (see, e.g.,, Madden et al, "Polypyrrole actuators: modeling and performance," at pp. 72-83), each of which is hereby incorporated by reference in its entirety.

Furthermore, networks of conductive polymers may also be employed. For example, it has been known to polymerize pyrrole in electroactive polymer networks such as poly(vinylchloride), poly(vinyl alcohol), NAFION®, a perfluorinated polymer that contains small proportions of sulfonic or carboxylic ionic finctional groups., available from E.I. DuPont Co., Inc. of Wilmington, Del. Electroactive polymers are also discussed in detail in commonly assigned copending U.S. patent application Ser. No. 10/763,825, the entire content of which is incorporated by reference herein. Existing electroactive polymers are also described in U.S. Pat. Nos. 6,515,077, 6,545,391, and 6,664,718. Also, electroactive polymers used in conjunction with medical devices are described in U.S. Pat. Nos. 6,514,237, 5,855,565, 6,679,836, U.S. Published Application No. 20050102017, U.S. Published Application No. 20040143160, U.S. Published Application No. 20040068161, and U.S. Pat. application Ser. No. 10/763,825. Existing catheter designs are described in U.S. Pat. No. 5,752,935 and E.P. 0619749.

In some embodiments, electrode 45 and electrode 46 are engaged to the EAP material and connected to voltage source 50. First electrode 45 is further engaged to flexible member 35. In some embodiments, the flexible member may also act as an electrode, thereby eliminating the need for first electrode 45. In at least one embodiment, the cathode of voltage source 50 is engaged to a first electrode 45 and the anode of voltage source 50 is engaged to a second electrode 46. When a voltage from voltage source 50 is supplied across first electrode 45 and second electrode 46, the EAP material expands, resulting in the petal, shown generally at 7, deflecting in a manner similar to the deflection depicted between FIG. 1 and FIG. 2.

Figure 6:
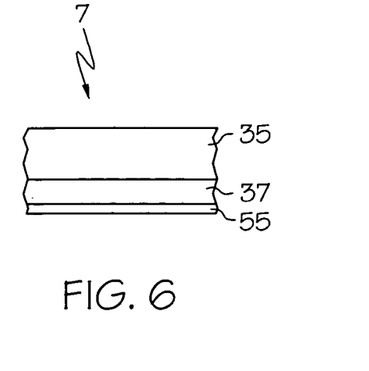
FIG. 6 is a side view of a portion of a petal comprised of flexible member, expandable polymer, and a fissurable coating.
Figure 7:
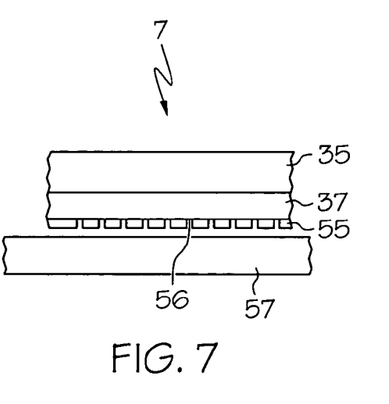
FIG. 7 is a side view of the portion of a petal comprised of a flexible member, expandable polymer, and fissurable coating shown in FIG. 6, with fissures in the coating.
Figure 8:
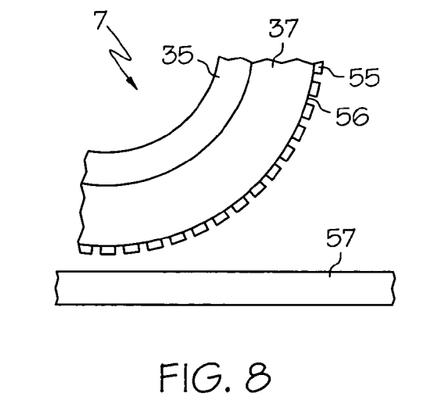
FIG. 8 is a side view of the portion of a petal comprised of a flexible member, expandable polymer, and fissurable coating shown in FIG. 7, with the expandable polymer expanded.

FIG. 6 shows a petal, shown generally at 7, comprising flexible member 35, expandable polymer 37, and fissurable coating 55. In at least one embodiment, fissurable coating 55 is designed to crack upon initial deployment of the stent. In some embodiments, fissurable coating 55 is designed to fissure upon introduction of a fluid, the fluid being introduced after the stent body is placed at the vessel bifurcation. FIG. 7 depicts petal 7 with fissurable coating 55 cracked such that fluid 57 will be absorbed by expandable polymer 37 through cracks 56. After sufficient fluid 57 has been absorbed by expandable polymer 37 through cracks 56, expandable polymer 37 expands from a low volume state to a high volume state, causing flexible member 35 to deflect. FIG. 8 shows the deflection of petal 7 after expandable polymer has expanded into a high volume state.

In some embodiments the stent comprises a therapeutic agent such that any fissuring of the fissurable coating releases the therapeutic agent. In one embodiment, the therapeutic agent is placed underneath the fissurable coating. In other embodiments, the therapeutic agent is placed on top of the fissurable coating.

Figure 9:
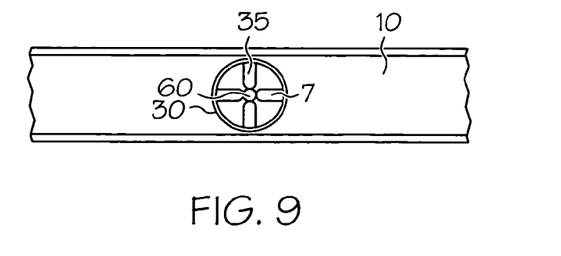
FIG. 9 is a top view of a stent with a branch body with an electrically frangible connector engaging flexible members.
Figure 10:
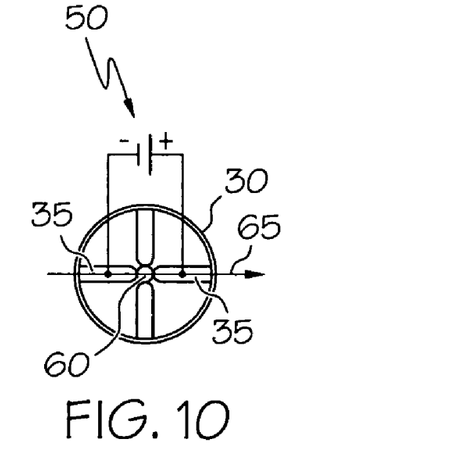
FIG. 10 is a top view of the branch body shown in FIG. 9 in an unexpanded configuration with a power source connected to flexible members held together in a first state by an electrically frangible connector.
Figure 11:
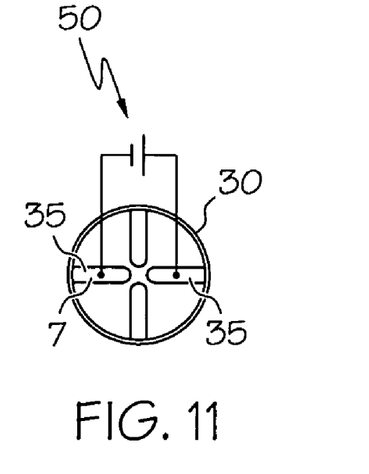
FIG. 11 is a top view of the branch body of FIG. 10 with the electrically frangible connector broken.
Figure 12:
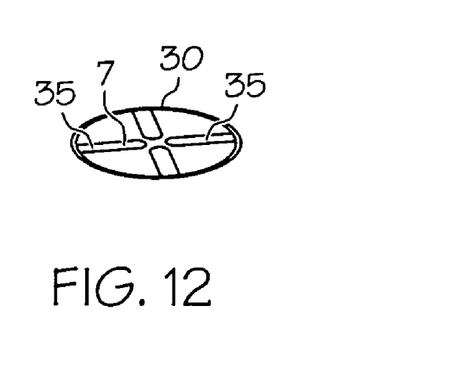
FIG. 12 is a perspective view of the branch body of FIG. 11 in an unexpanded configuration with flexible members.
Figure 13:
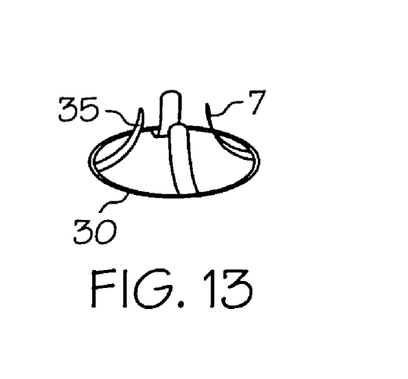
FIG. 13 is a perspective view of the branch body shown in FIG. 12 in an expanded configuration with flexible members.

In at least one embodiment, branch body 30 comprises flexible members 35. Branch body 30 is held in an unexpanded configuration via flexible members 35 engaged to an electrically frangible connector 60, as shown in FIG. 9, a top view of a bifurcated stent. Flexible members 35 are engaged to branch body 30, which is engaged to main body 10. Referring now to FIG. 10, a voltage source 50 is electrically connected across flexible members 35, engaged by electrically frangible connector 60. After a voltage is applied from voltage source 50, the connection formed between flexible members 35 by electrically frangible connector 60 is broken, as shown in FIG. 11. After electrically frangible connector 60 is broken, as shown in FIG. 12, flexible members 35 deflect, resulting in branch body 30 expanding to the expanded configuration shown in FIG. 13. In some embodiments, the electrically frangible connector shown in FIG. 10 is an electrolytic connector such that it is broken through an electrolytic process. In other embodiments, the electrically frangible connector shown in FIG. 10 is broken through overcurrent in a manner similar to a fuse. In some embodiments, the electrically frangible connector shown in FIG. 10 is a switch that opens through overcurrent, rather than breaking like a fuse, thereby separating the flexible members. Also, the switch is capable of being reset, unlike a fuse.

Figure 14:
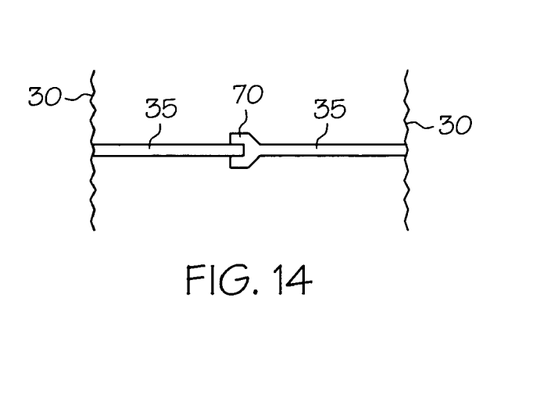
FIG. 14 is a side view of first and second flexible members releasably engaged to one another.
Figure 15:
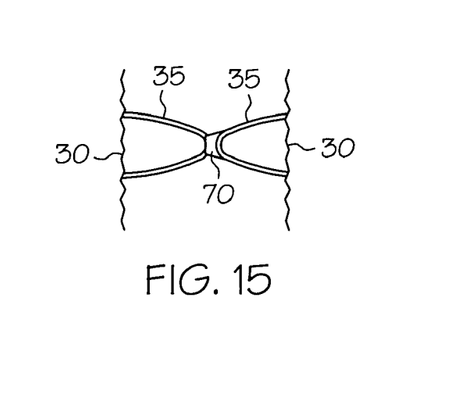
FIG. 15 is a top view of the first and second flexible members shown in FIG. 14.
Figure 16:
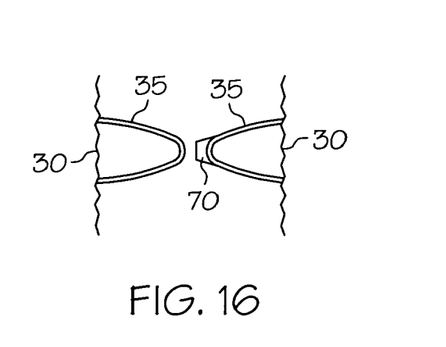
FIG. 16 is a top view of the first and second flexible members depicted in FIG. 15 after being disengaged.
Figure 17:
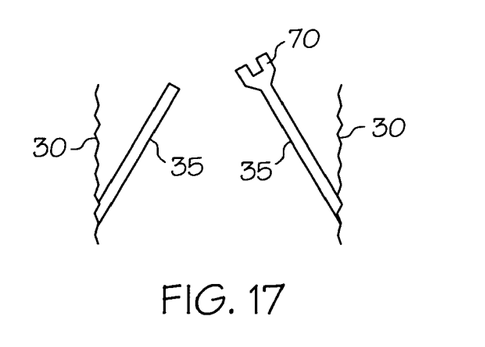
FIG. 17 is a side view of the first and second flexible members shown in FIG. 16, after being disengaged.

In another embodiment of the invention, flexible members 35 are held together through releasable engagement mechanism 70, as shown in side view FIG. 14 and top view FIG. 15. After delivery to the vessel bifurcation and as a result of initial expansion of the stent, the flexible members 35 begin to pull apart and separate from releasable engagement mechanism 70 such that releasable engagement mechanism 70 no longer holds flexible members 35, as depicted in FIG. 16. As the stent further expands, flexible members 35 deflect, as shown in FIG. 17.

In at least one embodiment, the connector is magnetically frangible. When the branch body is in the unexpanded configuration, a first flexible member is magnetically coupled to a second flexible member by the magnetically frangible connector. The magnetic coupling is achieved by a magnetic field. That is, when the stent is delivered, a magnetic field couples the flexible members together. In some embodiments, after the stent is delivered the magnetic field is removed, decoupling the flexible members so that they may deflect. FIG. 14 and FIG. 15 show an embodiment of a magnetically frangible connector 70. Connector 70 is magnetized, thereby coupling flexible members 35. When the magnetic field (not shown) is removed, connector 70 is demagnetized and flexible members 35 are no longer coupled, allowing branch body 30 to transition to an expanded configuration.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A stent for placement at a vessel bifurcation, the vessel having a main branch and a side branch, the stent having an expanded configuration and an unexpanded configuration, the stent comprising:

a substantially tubular main body defining a main lumen therethrough, and a branch body defining a branch lumen therethrough, the main lumen in fluid communication with the branch lumen, the branch body comprised of a first flexible member and a second flexible member, a connector engaging the first flexible member, the branch body being in the unexpanded state when the connector further engages the second flexible member, the branch body being in the expanded state when the second flexible member is disengaged from the connector, wherein the connector is electrically frangible, in the unexpanded state the electrically frangible connector being in electric communication with the first flexible member and the second flexible member, in the expanded state the electrically frangible connector being disengaged from at least one of the first flexible member and second flexible member as a result of excess current, and wherein after removal of the excess current, the electrically frangible connector is capable of again being in electric communication with the first flexible member and the second flexible member.

2. The stent of claim 1, wherein at least one of either the first flexible member or the second flexible member comprises an expandable polymer.

3. The stent of claim 2, wherein the expandable polymer is expanded by interacting with a fluid, the fluid being introduced into the body after the stent body is placed at the vessel bifurcation.

4. The stent of claim 2, wherein the expandable polymer comprises an electroactive polymer.

5. The stent of claim 1, wherein at least one of either the main body or branch body comprises a therapeutic agent.

6. The stent of claim 1, wherein at least one of either the first flexible member or the second flexible further comprises a fissurable coating.

7. The stent of claim 6, wherein the fissurable coating fissures upon interaction with a fluid, the fluid being introduced into the body after the stent body is placed at the vessel bifurcation.

8. The stent of claim 6, wherein the fissurable coating fissures upon initial deployment of the stent.

9. A stent for placement at a vessel bifurcation, the vessel having a main branch and a side branch, the stent having an expanded configuration and an unexpanded configuration, the stent comprising:

a substantially tubular main body defining a main lumen therethrough, and a branch body defining a branch lumen therethrough, the main lumen in fluid communication with the branch lumen, the branch body comprised of a first flexible member and a second flexible member, a connector engaging the first flexible member, the branch body being in the unexpanded state when the connector further engages the second flexible member, the branch body being in the expanded state when the second flexible member is disengaged from the connector, wherein the connector is magnetically frangible, the first flexible member being magnetically coupled to the second flexible member by the connector when the stent is in the unexpanded configuration, the first flexible member being magnetically decoupled from the second flexible member when the stent is in the expanded configuration.

10. The stent of claim 9, wherein at least one of either the first flexible member or the second flexible member comprises an expandable polymer.

11. A stent for placement at a vessel bifurcation, the vessel having a main branch and a side branch, the stent having an expanded configuration and an unexpanded configuration, the stent comprising:

a substantially tubular main body defining a main lumen therethrough, and a branch body defining a branch lumen therethrough, the main lumen in fluid communication with the branch lumen, the branch body comprised of a first flexible member and a second flexible member, a connector engaging the first flexible member, the branch body being in the unexpanded state when the connector further engages the second flexible member, the branch body being in the expanded state when the second flexible member is disengaged from the connector, wherein the connector is fixedly engaged to the first flexible member, when the stent is in the unexpanded state the connector is releasably engaged to the second flexible member, when the stent is in the expanded state the connector is disengaged from the second flexible member.

12. The stent of claim 11, wherein at least one of either the first flexible member or the second flexible member comprises an expandable polymer.

* * * * *